United States Patent
Chi et al.

(10) Patent No.: US 11,772,081 B2
(45) Date of Patent: Oct. 3, 2023

(54) PROCESSES FOR STABILIZING ANTIMONY CATALYSTS

(71) Applicant: Ascend Performance Materials Operations LLC, Houston, TX (US)

(72) Inventors: Y. T. Chi, Sugar Land, TX (US); Scott Moffatt, Pearland, TX (US); John Tjaden, Friendswood, TX (US); Chelsea Loyd, Pearland, TX (US); Lori Ables, Cantonment, FL (US)

(73) Assignee: Ascend Performance Materials Operations LLC, Houston, TX (US)

( * ) Notice: Subject to any disclaimer, the term of this patent is extended or adjusted under 35 U.S.C. 154(b) by 0 days.

(21) Appl. No.: 17/582,703

(22) Filed: Jan. 24, 2022

(65) Prior Publication Data
US 2022/0143583 A1    May 12, 2022

Related U.S. Application Data

(62) Division of application No. 16/797,869, filed on Feb. 21, 2020, now Pat. No. 11,235,313.
(Continued)

(51) Int. Cl.
*B01J 23/92* (2006.01)
*B01J 23/28* (2006.01)
(Continued)

(52) U.S. Cl.
CPC .............. *B01J 23/92* (2013.01); *B01J 23/28* (2013.01); *B01J 38/02* (2013.01); *C07C 253/24* (2013.01); *C07C 2531/34* (2013.01)

(58) Field of Classification Search
CPC .. B01J 23/92; B01J 23/28; B01J 38/02; C07C 253/24; C07C 2531/34
(Continued)

(56) References Cited

U.S. PATENT DOCUMENTS

| | | | |
|---|---|---|---|
| 3,341,471 | A | 9/1967 | Callahan et al. |
| 3,472,892 | A | 10/1969 | Callahan et al. |

(Continued)

FOREIGN PATENT DOCUMENTS

| | | |
|---|---|---|
| DE | 3311521 | 1/1984 |
| EP | 0889027 | 1/1999 |
| WO | 97/33863 | 9/1997 |

OTHER PUBLICATIONS

International Application No. PCT/US2020/019277, International Search Report and Written Opinion, dated Jun. 9, 2020, 11 pages.

*Primary Examiner* — Patricia L. Hailey
(74) *Attorney, Agent, or Firm* — COZEN O'CONNOR

(57) ABSTRACT

The present disclosure relates to a process for stabilizing an antimony ammoxidation catalyst in an ammoxidation process. The process may comprise providing an antimony ammoxidation catalyst to a reactor; reacting propylene with ammonia and oxygen in the fluidized bed reactor in the presence of the antimony ammoxidation catalyst to form a crude acrylonitrile product; and adding an effective amount of an antimony-containing compound to the antimony ammoxidation catalyst to maintain catalyst conversion and selectivity; wherein the antimony-containing compound has a melting point less than 375° C. The present disclosure also relates to catalyst compositions and additional processes using the antimony ammoxidation catalyst stabilized by an antimony-containing compound.

17 Claims, 2 Drawing Sheets

Related U.S. Application Data

(60) Provisional application No. 62/808,487, filed on Feb. 21, 2019.

(51) Int. Cl.
*B01J 38/02* (2006.01)
*C07C 253/24* (2006.01)

(58) Field of Classification Search
USPC .......................................... 502/20, 22, 353
See application file for complete search history.

(56) References Cited

U.S. PATENT DOCUMENTS

| | | | |
|---|---|---|---|
| 3,657,155 A | 4/1972 | Yoshino et al. | |
| 3,686,138 A | 8/1972 | Yoshino et al. | |
| 3,711,422 A | 1/1973 | Johnson et al. | |
| 3,882,159 A | 5/1975 | Callahan et al. | |
| 4,040,983 A * | 8/1977 | Innes | C01G 43/006 423/594.12 |
| 4,049,575 A * | 9/1977 | Sasaki | B01J 23/34 502/213 |
| 4,107,085 A | 8/1978 | Sasaki et al. | |
| 4,222,899 A | 9/1980 | Innes et al. | |
| 4,290,920 A | 9/1981 | Suresh et al. | |
| 4,296,046 A * | 10/1981 | Innes | C07C 253/26 558/326 |
| 4,330,429 A * | 5/1982 | Sasaki | B01J 23/94 558/324 |
| 4,419,267 A | 12/1983 | Sasaki et al. | |
| 4,504,599 A | 3/1985 | Sasaki et al. | |
| 4,536,483 A * | 8/1985 | Sasaki | B01J 27/30 423/376 |
| 4,757,038 A | 7/1988 | Sasaki et al. | |
| 4,855,275 A | 8/1989 | Suresh et al. | |
| 4,933,095 A | 6/1990 | Johnson et al. | |
| 4,954,467 A | 9/1990 | Johnson et al. | |
| 11,235,313 B2 * | 2/2022 | Chi | B01J 23/92 |

\* cited by examiner

PROCESSES FOR STABILIZING ANTIMONY CATALYSTS

CROSS-REFERENCE TO RELATED APPLICATION

This application is a divisional application of U.S. application Ser. No. 16/797,869, filed on Feb. 21, 2020, which claims priority to U.S. Provisional Application No. 62/808,487, filed Feb. 21, 2019, the entire contents and disclosures of which are incorporated herein by reference.

FIELD

The present disclosure relates to a process for stabilization of an antimony ammoxidation catalyst in ammoxidation process. In particular, the present disclosure relates to stabilization of an antimony ammoxidation catalyst by adding an antimony-containing compound to the antimony ammoxidation catalyst during the process.

BACKGROUND

Some processes for the production of acrylonitrile by ammoxidation of propylene are known in the art. The reaction is typically conducted over an ammoxidation catalyst. Various suitable catalysts are known as well. Typical metal oxide combinations include molybdenum-bismuth-iron and iron-antimony. In the interest of improving performance certain activators or promoter metals have been included as components of the ammoxidation catalysts. For example, iron, cobalt, nickel, manganese, cerium, uranium, tin, titanium, and copper have been included in the typical ammoxidation catalysts during the production thereof.

Further, for molybdenum-based ammoxidation catalysts, attempts have been made to carry out the reaction while supplying a molybdenum-containing material thereto in an effort to maintain catalyst efficiency. This technique, however, leaves room for improvement.

For example, U.S. Pat. No. 3,882,159 discloses a process, wherein a particle formed by supporting a molybdenum-containing material on silica is supplied to a fluidized bed catalyst containing molybdenum, bismuth, iron, cobalt and others, thereby restoring the catalyst efficiency. DE 3,311,521 discloses a process for reactivating molybdenum-containing catalyst is described, in which 0.25-2.5% by weight of a molybdenum compound having a particle size of 4 μm-1 mm is added to the catalyst to be regenerated. In this way it is possible, for example, to increase the yield in the production of acrylonitrile from about 65 to 73%.

WO 97/33863 disclose a process for preparing acrylonitrile or methacrylonitrile which comprises adding a molybdenum compound which is not supported on any carrier and which, during ammoxidation, can be converted to molybdenum oxide in such a manner that the atomic ratio y of molybdenum in an oxide catalyst represented by the general formula:

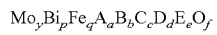

$Mo_yBi_pFe_qA_aB_bC_cD_dE_eO_f$ is kept between 1.02x and 1.12x (wherein x=1.5 p+q+a+c+ 1.5 d+1.5 e) as an activating agent to a fluidized bed reaction. These improvements have been effective only to some extent.

U.S. Pat. No. 4,290,920 discloses that antimony-based oxide complex catalysts are improved by adding to these catalysts an antimony-containing compound such as $Sb_2O_3$. U.S. Pat. No. 4,504,599 discloses that antimony-containing metal oxide catalysts are produced or activated by dry blending (a) a catalyst or catalyst precursor composed of an antimony-containing metal oxides composition containing antimony and at least one element selected from the group consisting of iron, cobalt, nickel, manganese, cerium, uranium, tin, titanium, and copper, and (b) elemental antimony or an antimony compound, and contacting the components (a) and (b) with each other at about 300° C. to about 1.000° C. in a non-reducing gas atmosphere for a period sufficient for the elemental antimony or antimony compound (b) to deposit on the catalyst or catalyst precursor (a).

U.S. Pat. No. 4,504,599 discloses antimony-containing metal oxide catalysts that are produced or activated by dry blending (a) a catalyst or catalyst precursor composed of an antimony-containing metal oxides composition containing antimony and at least one element selected from the group consisting of iron, cobalt, nickel, manganese, cerium, uranium, tin, titanium, and copper, and (b) elemental antimony or an antimony compound, and contacting the components (a) and (b) with each other at about 300° C. to about 1000° C. in a non-reducing gas atmosphere for a period sufficient for the elemental antimony or antimony compound (b) to deposit on the catalyst or catalyst precursor (a).

Even in view of these references, however, the need remains for processes that improve ammoxidation catalyst stability and provide for improvements in conversion and selectivity over time.

SUMMARY

The present disclosure relates to a process for stabilizing an antimony ammoxidation catalyst in an ammoxidation process, the process comprising: providing an antimony ammoxidation catalyst to a reactor; reacting propylene with ammonia and oxygen in the fluidized bed reactor in the presence of the antimony ammoxidation catalyst, which may further comprise molybdenum and/or a molybdenum oxide, to form a crude acrylonitrile product; and adding an effective amount, e.g., less than 2500 wppm per day, less than 2000 wppm per day, less than 1500 wppm per day, or less than 1000 wppm per day, of an antimony-containing compound, e.g., antimony triacetate, antimony oxides, or organoantimony compounds, or combinations thereof, preferably antimony triacetate, to the antimony ammoxidation catalyst to maintain catalyst conversion and selectivity. The antimony-containing compound has a melting point less than 375° C. The catalyst conversion may be maintained within 10% of a target conversion, e.g., within 5%, or may be at least 45% over a period of at least 1 year; the catalyst selectivity to acrylonitrile may be maintained within 10% of a target selectivity or may be at least 50% over a period of at least 1 year. The antimony-containing compound may be a solid and may have a low vapor pressure. The adding may comprise mixing replenishing antimony-containing ammoxidation catalyst with the antimony-containing compound and may be conducted at a temperature less than 300° C. and/or conducted upstream of the reactor, and/or conducted after an initial catalyst conditioning period. The process may further comprise the step of releasing antimony ammoxidation catalyst vapors from antimony ammoxidation catalyst in the reactor and/or vaporizing the antimony-containing compound to suppress the release of the antimony ammoxidation catalyst vapors. The adding may comprise adding antimony-containing compound directly into a catalyst hopper comprising replenishing antimony ammoxidation catalyst and then feeding the resultant replenishing antimony catalyst composition to the reactor; and/or mixing antimony-containing compound with replenishing antimony ammoxidation catalyst and then feeding the resultant replenishing antimony catalyst composition directly to the reactor; and/or dissolving antimony-containing compound in water to form an aqueous solution and then adding the aqueous solution to the reactor; or combinations thereof. The antimony-containing compound and the antimony ammoxidation catalyst may comprise less than 1 wt % potassium, lithium, sodium, cesium, indium, rubidium, samarium, calcium, strontium, barium or tellurium. The adding step may further comprise adding an effective amount of a molybdenum-containing compound to the antimony ammoxidation catalyst and the molybdenum-containing compound comprises ammonium molbydates, metal molybdates, molybdenum oxides, or molybdenum acetates, or combinations thereof and/or adding at least one additive to the fluidized bed reactor.

In some cases, the disclosure relates to an antimony-containing ammoxidation catalyst composition comprising an antimony-containing ammoxidation catalyst; and an antimony-containing compound, e.g, antimony triacetate; wherein the antimony-containing compound has a melting point less than 375° C. The catalyst may further comprise a molybdenum and a molybdenum-containing compound, e.g., ammonium heptamolbydate.

In some embodiments, the disclosure relates to a process for producing acrylonitrile, the process comprising providing an antimony ammoxidation catalyst to a reactor; reacting propylene with ammonia and oxygen in the reactor in the presence of the antimony ammoxidation catalyst; measuring catalyst conversion of propylene and/or catalyst selectivity to acrylonitrile; and when conversion and/or selectivity is decreases, adding an effective amount of an antimony-containing compound to the antimony ammoxidation catalyst to maintain catalyst conversion and selectivity; wherein the antimony-containing compound has a melting point less than 375° C.

In some embodiments, the disclosure relates to a process for stabilizing an antimony-containing catalyst in a reactor, the process comprising providing an antimony-containing catalyst to a reactor; conducting a reaction in the presence of the antimony-containing catalyst, wherein the reaction is an ammoxidation reaction, or an oxidation reaction, or a combination thereof; and adding an effective amount of an antimony-containing compound to the reactor. The reaction may be the ammoxidation reaction, and the reaction may be conducted in the presence of ammonia and oxygen. The reaction may be the oxidation reaction of a hydrocarbon feedstock, and the reaction is conducted in the presence of oxygen, and the hydrocarbon may comprise olefins, alcohols, alkanes, ketones, aldehydes, carboxylic acids, esters, ethers, or nitriles, or derivatives thereof, or combinations thereof. The adding further comprises adding a molybdenum-containing compound to the reactor.

BRIEF DESCRIPTION OF THE DRAWINGS

The disclosure is described in detail below with reference to the appended drawings, wherein like numerals designate similar parts.

DETAILED DESCRIPTION

Introduction

Figure 1:
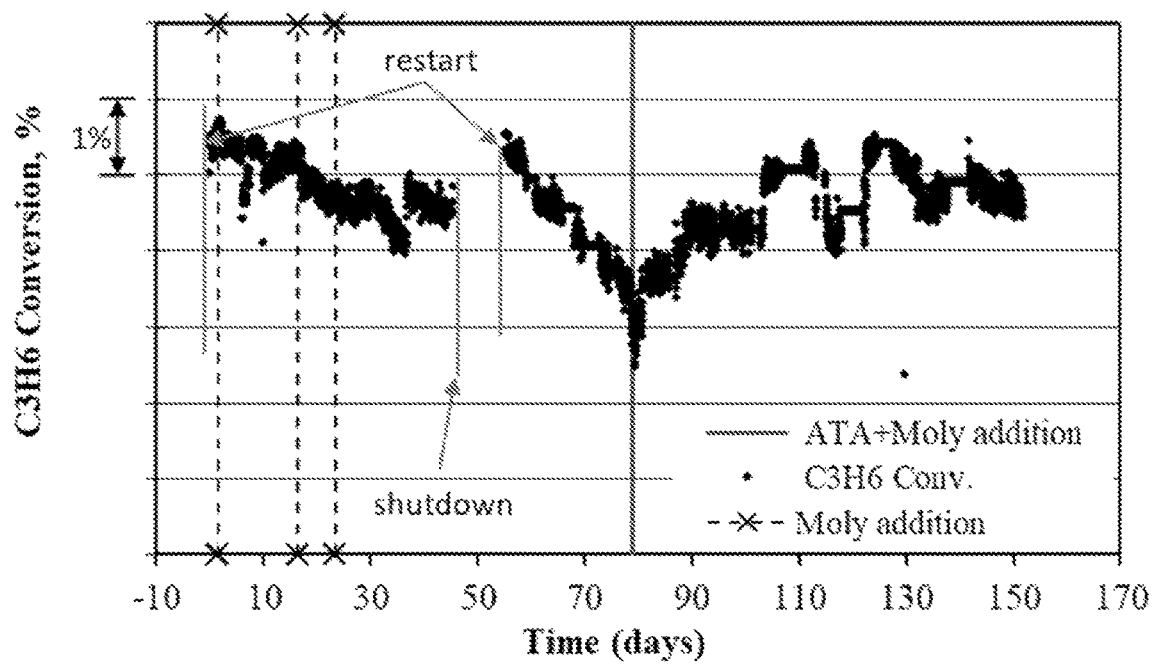
FIG. 1 shows the conversion of propylene in accordance with embodiments of the present disclosure.

As noted above, some ammoxidation catalysts are known, as are some methods for improving the performance and stability of these catalysts by adding activators or promoters as components of the catalyst. For example, antimony-based oxide complex catalysts may be improved by adding to these catalysts an antimony-containing compound such as $Sb_2O_3$. Such compounds may be incorporated directly into the catalyst through a series of inefficient process steps, e.g., contacting at about 300° C. to about 1000° C. in a non-reducing gas atmosphere, to produce final catalyst for use. The result being that the compound is deposited directly on the catalyst or catalyst precursor for use.

The inventors have found that, when in use at high temperatures of an ammoxidation reaction, portions of the ammoxidation catalysts may vaporize, and that the resultant vapor (containing catalytic components) may be lost through exhaust vents. The loss of these components leads to catalyst degradation and reduction of catalyst performance and stability.

It has now been discovered that the addition of specific antimony-containing compounds, e.g., those having lower melting points, have been shown to provide for significant improvements in catalyst degradation loss. Without being bound by theory, it is postulated that these antimony-containing compounds, when provided to the ammoxidation catalyst in the reactor, e.g., not as a part of the original catalyst, vaporize more readily than the antimony ammoxidation catalyst. The vapor produced by the antimony-containing compounds surprisingly has been found to suppress the vaporization of the ammoxidation catalyst, which, in turn, retards or eliminates ammoxidation catalyst degradation via vaporization. In addition, the vaporization suppression has been found to reduce or eliminate resultant antimony-containing phase migration, transformation, and/or destruction. Importantly, the particular antimony-containing compounds may not be added as a component of the ammoxidation catalyst when the catalyst is made, e.g., may not be impregnated onto the ammoxidation catalyst, as has been done in some conventional catalyst preparation processes. Rather, the antimony-containing compounds are provided once the ammoxidation production process has begun so as to replenish the (degraded) ammoxidation catalyst. It is believed that providing the antimony-containing compounds to the ammoxidation process, and not as a component of the catalyst (or makeup catalyst added to the reactor), allows the antimony-containing compounds to better vaporize, and, in turn, to better suppress the vaporization of the ammoxidation catalyst.

Although there may be some teachings relating to the addition of molybdenum compounds to an originally-charged molybdenum catalyst, these teachings are not applicable to antimony catalysts. In some cases, it has been found that the addition of ammonium heptamolybdate (AHM) (alone), was ineffective in stabilizing the catalyst, e.g., in terms of acrylonitrile yield and surface area. Further, the majority of the molybdenum teachings relate specifically to molybdenum-based catalysts with a molybdate or a polymolybdate, not antimony or antimonate-based catalysts. Further, in some plant environments, the addition of molybdenum components to an originally-charged antimony catalyst has been tested, and the molybdenum components led to only (at best) minor improvements—certainly not the significant improvements recognized herein with the addition of antimony-containing compounds.

In addition, most conventional molybdenum-based catalysts have a scheelite-type structure, and the teachings relating to these catalysts are specific to these structures. In contrast, many antimony ammoxidation catalyst have a rutile structures, not scheelite-type structures. And it is well-known that there are significant differences between scheelite-type structures and rutile-type structures. Exemplary differences include, but are not limited to atomic arrangement or atomic structure, crystal unit cell, crystal face cleavage, crystal twinning, and crystal planes and facets, et al. Importantly, as it relates to heterogeneous catalysis including the ammoxidation reactions of the present disclosure, the catalytic reaction typically occurs on the surface of the solid catalyst. And the interaction between exposed facets from the catalyst and reactant molecules significantly affects or determines the catalyst performance. Because many of the conventional teachings relate to molybdenum catalysts and scheelite-type structure, these teachings are not applicable and/or relevant to the present disclosure, which related antimony ammoxidation catalysts, e.g., with rutile structure.

In some cases, because lower melting point antimony-containing compounds are used, the resultant vaporization and suppression occurs more readily, the antimony-containing compounds may beneficially be employed in specific (low) amounts, e.g., less than 1000 wppm per charge, e.g., 1000 wppm per day of operation, based on the total weight of the antimony-containing ammoxidation catalyst, which advantageously allows for lesser amounts of antimony-containing compounds to be used to achieve suitable results. Conventional processes have employed higher melting point temperature antimony-containing compounds, and as such, have been required to employ them in much higher amounts, e.g., greater than 1000 wppm, which contributes to process inefficiencies. For example, the use of higher amounts may allow the antimony-containing compounds to escape from the reaction system, thus resulting in inefficient consumption. Also, the antimony-containing compounds may detrimentally precipitate or accumulate inside of the reactor or adheres to a heat exchanger, thereby causing operational problems.

In some embodiments, this disclosure relates to a process for stabilizing an antimony ammoxidation catalyst in an ammoxidation process (by suppressing catalyst component vaporization). In some cases, the disclosure relates more broadly to catalyst stabilization in other reactions that may employ an antimony catalyst, e.g., an oxidation reaction. The process comprises the steps of providing an antimony (ammoxidation) catalyst to a reactor and conducting an ammoxidation reaction, e.g., reacting propylene with ammonia and oxygen, in the reactor in the presence of the antimony ammoxidation catalyst to form a crude acrylonitrile product. The process further comprises the step of adding an effective amount of an antimony-containing compound to the antimony ammoxidation catalyst to maintain catalyst conversion and selectivity.

The antimony-containing compound has a low melting point, e.g., a melting point less than 375° C., less than 350° C., less than 325° C., less than 300° C., less than 275° C., less than 250° C., less than 225° C., less than 200° C., less than 175° C., or less than 150° C. In terms of lower limits, the antimony-containing compound may have a melting point of at least 5° C., e.g., at least 10° C., at least 25° C., at least 50° C., or at least 55° C.

In some embodiments, the an effective amount of antimony-containing compound is employed. For example, the antimony-containing compound may be added in an amount less than 1000 wppm per day, based on the total weight of the antimony-containing ammoxidation catalyst, e.g., less than 1000 wppm per day, less than 800 wppm per day, less than 600 wppm per day, less than 500 wppm per day, less than 400 wppm per day, less than 300 wppm per day, less than 200 wppm per day, less than 100 wppm per day, less than 75 wppm per day, less than 50 wppm per day, less than 40 wppm per day, less than 30 wppm per day, or less than 20 wppm per day. In terms of lower limits, the antimony-containing compound may be added in an amount greater than 1 wppm per day, e.g., greater than 2 wppm per day, greater than 4 wppm per day, greater than 5 wppm per day, greater than 6 wppm per day, greater than 8 wppm per day, greater than 10 wppm per day, greater than 12 wppm per day, greater than 15 wppm per day, greater than 20 wppm per day, or greater than 25 wppm per day. In terms of ranges, the antimony-containing compound may be added in an amount ranging from 1 wppm to 1000 wppm per day, e.g., from 2 wppm to 800 wppm per day, from 3 wppm to 500 wppm per day, from 3 wppm to 300 wppm per day, from 3 wppm to 100 wppm per day, from 2 wppm to 50 wppm per day, from 5 wppm to 40 wppm per day, from 10 wppm to 30 wppm per day, or from 15 wppm to 25 wppm per day.

The addition may also be characterized in terms of elemental antimony. For example, the antimony-containing compound may be added such that elemental antimony is added in an amount less than 500 wppm per day, based on the total weight of the antimony-containing ammoxidation catalyst, e.g., less than 300 wppm per day, less than 100 wppm per day, less than 50 wppm per day, less than 35 wppm per day, less than 25 wppm per day, less than 20 wppm per day, less than 15 wppm per day, less than 13 wppm per day, or less than 12 wppm per day. In terms of ranges, the antimony-containing compound may be added such that elemental antimony is added in an amount greater than 0.01 wppm per day, e.g., greater than 0.05 wppm per day, greater than 0.1 wppm per day, greater than 0.5 wppm per day, greater than 1 wppm per day, greater than 1.5 wppm per day, greater than 2 wppm per day, greater than 2.5 wppm per day, greater than 3 wppm per day, greater than 3.5 wppm per day, greater than 4 wppm per day, greater than 5 wppm per day, or greater than 7 wppm per day. In terms of ranges, the antimony-containing compound may be added such that elemental antimony is added in an amount ranging from 0.01 wppm to 500 wppm per day, e.g., from 0.05 wppm to 300 wppm per day, from 0.1 wppm to 100 wppm per day, from 0.5 wppm to 50 wppm per day, from 1 wppm to 25 wppm per day, from 2 wppm to 20 wppm per day, from 3 wppm to 15 wppm per day, from 4 wppm to 12 wppm per day, or from 5 wppm to 10 wppm per day.

As a result, catalyst activity and stability are improved. In some cases, because of the aforementioned addition of the antimony-containing compound, catalyst conversion may be maintained within 10% of a target conversion over a period of at least 1 year, e.g., within 7%, within 5%, within 4%, within 3%, within 2%, or within 1%. In some cases, catalyst selectivity to acrylonitrile is maintained within 10% of a target selectivity over a period of at least 1 year, e.g., within 7%, within 5%, within 4%, within 3%, within 2%, or within 1%.

In some embodiments, the catalyst conversion is (on average) at least 45% (over a period of at least 1 year), e.g., at least 50%, at least 60%, at least 70%, at least 80%, at least 90%, at least 95%, at least 99%, at least 99.5%, or at least 99.9%. In terms of ranges, the catalyst conversion may range (on average) from 45% to 99.9% (over a period of at least 1 year), e.g., from 50% to 99.9%, from 60 to 99.9%, from 70% to 99.9%, from 80% to 99.9%, from 90% to 99.9%, from 90% to 99.5%, from 95% to 99.9%, or from 95% to 99.5%. These conversion ranges and limits are significantly higher than those achieved via conventional processes, see for example U.S. Pat. No. 6,156,920 (~20%); 7,754,910 (~90%); and 8,921,257 (~41%).

In some embodiments, the catalyst selectivity to acrylonitrile is (on average) at least 50% (over a period of at least 1 year), e.g., at least 60%, at least 65%, at least 70%, at least 75%, at least 80%, or at least 85%. In terms of ranges, the catalyst selectivity to acrylonitrile may range (on average) from 50% to 99.9% (over a period of at least 1 year), e.g., from 55% to 99.9%, from 65 to 99.9%, from 65% to 90%, from 70% to 99.9%, from 65% to 85%, from 67% to 82%, or from 70% to 81%.

In some embodiments, the catalyst selectivity to cyanide is (on average) at least 1% (over a period of at least 1 year), e.g., at least 2%, at least 3%, at least 4%, at least 5%, at least 6%, or at least 7%. In terms of ranges, the catalyst selectivity to cyanide may range (on average) from 1% to 30% (over a period of at least 1 year), e.g., from 2% to 25%, from 3% to 20%, from 3% to 15%, from 4% to 12%, or from 6% to 10%.

In some embodiments, the stability of the catalyst surface area is improved. For example, catalyst surface may vary only +/−25%, e.g., +/−20%, +/−18%, +/−15%, +/−13%, +/−10%, +/−8%, or +/−5%.

As noted above, the inventors believe that, when these antimony-containing compounds are added to the reactor (directly or indirectly), these antimony-containing compounds vaporize much more easily than the antimony present in the ammoxidation catalyst. It has been discovered that this additional vapor present in the reactor has a suppressive effect on the vapor leaving the originally-charged catalyst, which, in turn, retards or eliminates ammoxidation catalyst degradation via vaporization.

In some cases, the process further comprises the step of vaporizing at least a portion of the originally-charged antimony oxidation catalyst to form antimony ammoxidation catalyst vapors, e.g., releasing antimony ammoxidation catalyst vapors, e.g., antimony vapor, from the antimony ammoxidation catalyst in the reactor.

It is believed that the heat of the reaction causes ammoxidation catalyst components, e.g., antimonates and antimony oxides, in the originally-charged catalyst to migrate outwardly from the bulk of the catalyst toward the outer surface thereof. This phenomenon leads to detrimental degradation of the antimonate and antimony oxides, phase destruction and reconstruction, and volatilization and/or sublimation. The loss of these antimony ammoxidation catalyst vapors degrades the ammoxidation catalyst, e.g., causes deactivation and/or performance deterioration.

To reduce this degradation, the process may further comprise the step of vaporizing the antimony-containing compound to produce antimony-containing compound vapors. As noted above the antimony-containing compound vapors have surprisingly been found to suppress the release of the antimony ammoxidation catalyst vapors, thus eliminating or reducing ammoxidation catalyst degradation.

Importantly, the addition of the antimony-containing compound is a step in the ammoxidation process, and the addition of the antimony-containing compound is not provided to the ammoxidation catalyst when it is made or manufactured. Stated another way, the addition of the antimony-containing compound is directly added to the ammoxidation process. In some cases, the addition of the antimony-containing compound is conducted after an initial catalyst conditioning period, which is after at least some of the reactants have been passed over the ammoxidation catalyst in the reactor. As discussed herein, the addition of the antimony-containing compound serves to suppress loss of the originally-charged catalyst and to maintain catalyst conversion and selectivity, as the ammoxidation reaction proceeds. In some cases, at least a portion of the antimony-containing compound is not added to or does not accumulate on the originally-charged catalyst, instead at least a portion of the antimony-containing compound is provided so that it adds a second vaporizable material to the reactor. Accordingly, the antimony-containing compound may advantageously be employed in much smaller amounts, as compared to situations where the antimony-containing compound is employed to become a part of the originally-charged catalyst.

In some cases, the addition of the antimony-containing compound is conducted, upstream of the ammoxidation reactor. In one embodiment, the addition of the antimony-containing compound is conducted (directly) in a catalyst hopper. A catalyst hopper is a unit of the ammoxidation process that holds replenishing antimony ammoxidation catalyst for replenishing the originally-charged ammoxidation catalyst. Thus, the process may comprise the step of mixing replenishing antimony-containing ammoxidation catalyst with the antimony-containing compound. The addition of the antimony-containing compound upstream of the reactor, e.g., in the hopper, provides for process efficiencies such as low temperature/pressure operation. The antimony-containing compound may be combined with the replenishing antimony ammoxidation catalyst (in the hopper), then fed (directly or indirectly) to the reactor for vapor suppression/replenishment. Beneficially, the hopper is typically an existing part of the process, thus there is not additional capital cost associated with new equipment.

In other cases, the antimony-containing compound may be mixed with the replenishing antimony ammoxidation catalyst (at a location other than the hopper) and then fed (directly or indirectly) to the reactor. In some cases, the antimony-containing compound may be dissolved in non-acidic, environmentally-friendly solvents, e.g., water, to form an aqueous solution and then added (directly or indirectly) to the reactor. These addition options may be used in conjunction with one another. These methods advantageously avoid harsh solvents, e.g., acids such as nitric acid and the inefficiencies of having to produce a slurry.

In other cases, the antimony-containing compounds, especially those in liquid forms may be vaporized and then fed to the reactor. Continuous feeding, e.g., via a feed pump, and using carrier gas, e.g., air, are optional techniques as well.

In some embodiments the adding of the antimony-containing compounds is conducted at a low temperatures, e.g., temperature less than 300° C., less than 290° C., less than 275° C., less than 250° C., or less than 200° C. In some cases the adding is conducted at room temperature. This low temperature addition eliminates the need for additional heating steps, which contributes to the overall process efficiency. Also, the use of specific antimony-containing compounds allows these compounds to be employed in much smaller amounts, e.g., less than 1000 wppm or less than 100 wppm, which also contributes to process efficiencies.

Antimony-Containing Compound

The antimony-containing compounds may vary widely as long as they meet the aforementioned melting point criterion. For example, antimony-containing compounds may comprise antimony acetates, antimony oxides, or organoantimony compounds, or combinations thereof. In some embodiments, antimony-containing compounds comprise antimony acetates, e.g., antimony triacetate (ATA). In some aspects, the antimony-containing compound may contain less than three phenyl groups, e.g., less than 2 phenyl groups, or no phenyl groups.

In some cases, the antimony-containing compound may comprise metallorganics and their precursors in various forms. In some embodiments, the antimony-containing compound may comprise antimony methoxide, methacryloxydiphenylantimony, triphenylantimony, tris(o-tolyl)antimony, tris(p-tolyl)antimony, poly(antimony ethylene glycoxide), potassium antimonyl tartrate trihydrate, potassium antimony tartrate hydrate, potassium antimony oxide tartrate trihydrate, antimony n-butoxide, antimony ethoxide, tris(dimethylamino)antimony, tris(trimethylsilyl)antimony, antimony isopropoxide, antimony propoxide, or antimony trimethylsiloxide, or combinations thereof.

In some embodiments, antimony-containing compounds such as ATA have been found to have significant advantages over the originally-charged catalyst in terms of volatility (tendency of a solid/liquid to readily change from solid/liquid to vapor state, evaporate). In addition the use of such compounds (versus charged catalysts) also brings efficiencies relating to the elimination of the need for catalyst improvement steps such as mixing of raw materials, synthesis in precipitation, deposition or impregnation, drying, and calcination process operations.

In some cases, the antimony-containing compounds may include the high antimony-containing ammoxidation catalyst and/or makeup catalysts. And these compounds may be added, optionally along with other antimony-containing compounds, as discussed herein, and not as a component of the originally-charged catalyst.

In some cases, the antimony-containing compound is a solid, e.g., a powder. These powders are capable of vaporizing once exposed to the high temperatures of the reactor. Beneficially, the use of such powders eliminates the need for dissolution in harmful or environmentally-unfriendly solvents, e.g., acids such as nitric acid, or for formation of slurries, thus providing for improvements in process efficiencies. Conventional methods require the use of corrosive nitric acid solutions for impregnation. With the aforementioned solid antimony-containing compounds, the harmful effects of these solvents may be minimized or avoided.

In some cases, the antimony-containing compound excludes high melting point or high vapor pressure compounds. For example, in some embodiments, the antimony-containing compound does not comprise antimony oxides, e.g., antimony trioxide, biantimony tetraoxide, or $Sb_2O_5$, or combinations thereof.

In some embodiments, the antimony-containing compound has a low vapor pressure. In some cases, the antimony-containing compound does not comprise higher vapor pressure compounds, e.g., antimony trioxide.

In some embodiments, the antimony ammoxidation catalyst (and the antimony-containing compound) comprise low amounts, if any, of unnecessary additives, thus eliminating the need. For example, the antimony-containing ammoxidation catalyst may comprise low amounts, if any, potassium, lithium, sodium, cesium, indium, rubidium, samarium, calcium, strontium, barium, or tellurium. In some cases, the antimony-containing ammoxidation catalyst (and the antimony-containing compound) comprise less than 1 wt % of these compounds, either individually or combined, based on the total weight of the antimony-containing ammoxidation catalyst or the antimony-containing compound, respectively, e.g., less than 0.5 wt %, less than 0.3 wt %, less than 0.1 wt %, less than 0.05 wt %, or less than 0.01 wt %.

The inventors have also found that, in addition to the antimony-containing compound, it is unexpectedly beneficial to also add a molybdenum-containing compound. Thus, the process (the adding step) may further comprise adding an effective amount of a molybdenum-containing compound to the antimony ammoxidation catalyst. The molybdenum-containing compound may be added in the manner and amounts disclosed herein with respect to the antimony-containing compound.

The molybdenum-containing compound may vary widely. In some cases, the molybdenum-containing compound comprises ammonium molbydates (ammonium heptamolbydate, ammonium dimolybdate), metal molybdates (bismuth molybdate, iron (II) molybdate, manganese (II) molybdate), molybdenum oxides (molybdenium trioxide, molybdic acid), or molybdenum acetates (molybdenum (II) acetate), or combinations thereof.

Also, other processing additives may be added to the reactor (along with the antimony-containing compound). Suitable processing additives are well known and include, but are not limited to, inert fines.

The disclosure also relates to an antimony ammoxidation catalyst composition for replenishing an originally-charged catalyst. The replenishing antimony ammoxidation catalyst comprises an antimony-containing ammoxidation catalyst and the aforementioned antimony-containing compounds. The antimony-containing compound has a melting point less than 375° C., as discussed above. In some cases, the antimony-containing compound in the replenishing antimony ammoxidation catalyst is antimony triacetate. The replenishing antimony ammoxidation catalyst may further comprise the aforementioned molybdenum-containing compounds, e.g., ammonium heptamolbydate.

In addition, the disclosure relates to a process for producing acrylonitrile. The process comprises the steps of providing an antimony ammoxidation catalyst to a reactor and reacting propylene with ammonia and oxygen in the reactor in the presence of the antimony ammoxidation catalyst. The process further comprises the step of measuring catalyst properties, e.g., conversion of propylene and/or catalyst selectivity to acrylonitrile. As the process proceeds, the originally-charged catalyst may degenerate. When the measured properties change, are reduced by a certain predetermined limit, the antimony-containing compound may be added to the reactor, as disclosed herein. In some cases, the addition may take place when conversion and/or selectivity are reduced by at least 0.1%, e.g., at least 0.2%, at least 0.5%, at least 1%, at least 3%, at least 5%, or at least 10%.

Also, as noted above, the disclosure may relate more broadly to processes and/or reactions other than the ammoxidation reaction. For example the disclosure also relates to processes that employ antimony catalysts, e.g., an oxidation reaction.

In some embodiments, the disclosure relates to a process for stabilizing an antimony-containing catalyst in a reactor. The process comprises the step of providing an antimony-containing catalyst to a reactor and conducting a reaction in the presence of the antimony-containing catalyst. For example, the reaction may be an ammoxidation reaction, or an oxidation reaction, or a combination thereof. To achieve the benefits disclosed herein, the process may further comprise the step of adding an effective amount of an antimony-containing compound to the reactor to maintain catalyst conversion and selectivity. The process may further comprise adding a molybdenum-containing compound to the reactor.

In cases where the reaction is the ammoxidation reaction, the reaction may be conducted in the presence of ammonia and oxygen. In cases where the reaction is an oxidation reaction of a hydrocarbon feedstock, the reaction may be conducted in the presence of oxygen. Exemplary hydrocarbons include olefins, alcohols, alkanes, ketones, aldehydes, carboxylic acids, esters, ethers, or nitriles, or derivatives thereof, or combinations thereof.

Antimony Ammoxidation Catalyst

The antimony ammoxidation catalyst may vary widely, and many conventional ammoxidation catalysts are known. For example, the antimony ammoxidation catalyst may be any of the known antimony-containing metal oxide catalysts described in the above-mentioned patents. The antimony ammoxidation catalyst may containing antimony (oxide) and an oxide of at least one metal selected from the group consisting of iron, cobalt, nickel, manganese, cerium, uranium, tin, titanium and copper.

In some embodiments, the antimony ammoxidation catalyst is a composition represented by the following empirical formula:

$$Me_a Sb_b X_c Q_d R_e O_f (SiO_2)_g$$

where:
Me is at least one element selected from the group consisting of Fe, Co, Ni, Mn, Ce, U, Sn, Ti, and Cu
X is at least one element selected from the group consisting of V, Mo, and W
Q is at least one element selected from the group consisting of Li, Na, K, Rb, Cs, Be, Mg, Ca, Sr, Ba, Y, La, Th, Zr, Hf, Nb, Ta, Cr, Re, Ru, Os, Rh, Ir, Pd, Pt, Ag, Zn, Cd, Al, Ga, In, Tl, Ge, Pb, As, S, and Se
R is at least one element selected from the group consisting of B, P, Te, and Bi
the subscripts a, b, c, d, e, f, and g denote the atomic ratio in the following range:
a=5 to 15,
b=5 to 100,
c=0 to 15,
d=0 to 50,
e=0 to 10,
f=a number corresponding to the oxides formed by the combination of the above components, and
g=0 to 200.

These catalysts may be used as such or may be supported on a carrier such as silica, alumina, silica-alumina, silica-titania, titania, or zirconia.

These oxide compositions can be prepared by using known methods disclosed in U.S. Pat. Nos. 3,341,471, 3,657,155, 3,686,138 and 4,107,085, the entire contents and disclosures of which are incorporated herein by reference.

In some embodiments, the antimony ammoxidation catalyst has a rutile structure. The antimony ammoxidation catalyst does not have a scheelite-type structure. As noted above, the references and teachings that relate to the addition of molybdenum compounds to an originally-charged molybdenum catalyst apply to molybdenum catalysts having an entirely different crystalline structure, and, accordingly, are not applicable and/or relevant to the present disclosure, which related antimony ammoxidation catalysts, e.g., with rutile structure.

In some embodiments, the process for acrylonitrile production process may be carried out via conventional means. As one example, the acrylonitrile production process may be conducted in a fluidized bed reactor. Accordingly, the ammoxidation catalyst is additionally required to have physical properties suitable for the fluidized bed reaction. That is, it is additionally required that its bulk density, particle strength, attrition resistance, specific surface area, fluidity and others are suitable.

The reaction may be carried out at a reaction temperature ranging from 370° C. to 500° C., e.g., from 370° C. to 500° C., and at a reaction pressure of from atmospheric pressure to 500 kPa. Contact time may range from 0.1 to 20 seconds, e.g., from 1 second to 20 seconds.

EMBODIMENTS

The following embodiments are contemplated. All combinations of features and embodiments are contemplated.

Embodiment 1: A process for stabilizing an antimony ammoxidation catalyst in an ammoxidation process, the process comprising: providing an antimony ammoxidation catalyst to a reactor; reacting propylene with ammonia and oxygen in the fluidized bed reactor in the presence of the antimony ammoxidation catalyst to form a crude acrylonitrile product; and adding an effective amount of an antimony-containing compound to the antimony ammoxidation catalyst to maintain catalyst conversion and selectivity; wherein the antimony-containing compound has a melting point less than 375° C.

Embodiment 2: the embodiment of embodiment 1, wherein the catalyst conversion is maintained within 10% of a target conversion over a period of at least 1 year.

Embodiment 3: the embodiment of embodiment 1 or 2, wherein the catalyst selectivity to acrylonitrile is maintained within 10% of a target selectivity over a period of at least 1 year.

Embodiment 4: the embodiment of any of embodiments 1-3, wherein the catalyst conversion is at least 45% over a period of at least 1 year.

Embodiment 5: the embodiment of any of embodiments 1-4, wherein the catalyst selectivity to acrylonitrile is at least 50% over a period of at least 1 year.

Embodiment 6: the embodiment of any of embodiments 1-5, wherein the effective amount of antimony-containing compound is less than 1000 wppm per day, based on the total weight of the antimony-containing ammoxidation catalyst.

Embodiment 7: the embodiment of any of embodiments 1-6, wherein the effective amount of antimony-containing compound is less than 1000 wppm per day, based on the total weight of the antimony-containing ammoxidation catalyst, and wherein catalyst conversion is maintained to be within 5% of a target conversion over a period of at least 1 year.

Embodiment 8: the embodiment of any of embodiments 1-7, wherein the antimony-containing compound is a solid.

Embodiment 9: the embodiment of any of embodiments 1-8, wherein the antimony-containing compound has a low vapor pressure.

Embodiment 10: the embodiment of any of embodiments 1-9, wherein the adding is conducted at a temperature less than 300° C.

Embodiment 11: the embodiment of any of embodiments 1-10, wherein the antimony-containing compound comprises an antimony acetate.

Embodiment 12: the embodiment of any of embodiments 1-11, further comprising the step of releasing antimony ammoxidation catalyst vapors from antimony ammoxidation catalyst in the reactor.

Embodiment 13: the embodiment of any of embodiments 1-12, further comprising the step of vaporizing the antimony-containing compound to suppress the release of the antimony ammoxidation catalyst vapors.

Embodiment 14: the embodiment of any of embodiments 1-13, wherein the adding is conducted upstream of the reactor.

Embodiment 15: the embodiment of any of embodiments 1-14, wherein the adding is conducted after an initial catalyst conditioning period.

Embodiment 16: the embodiment of any of embodiments 1-15, wherein the adding comprises mixing replenishing antimony-containing ammoxidation catalyst with the antimony-containing compound.

Embodiment 17: the embodiment of any of embodiments 1-16, wherein the adding comprises: adding antimony-containing compound directly into a catalyst hopper comprising replenishing antimony ammoxidation catalyst and then feeding the resultant replenishing antimony catalyst composition to the reactor; or mixing antimony-containing compound with replenishing antimony ammoxidation catalyst and then feeding the resultant replenishing antimony catalyst composition directly to the reactor; or dissolving antimony-containing compound in water to form an aqueous solution and then adding the aqueous solution to the reactor; or combinations thereof.

Embodiment 18: the embodiment of any of embodiments 1-17, wherein the antimony-containing compound and the antimony ammoxidation catalyst comprises less than 1 wt % potassium, lithium, sodium, cesium, indium, rubidium, samarium, calcium, strontium, barium or tellurium.

Embodiment 19: the embodiment of any of embodiments 1-18, wherein the antimony-containing ammoxidation catalyst further comprises molybdenum and/or a molybdenum oxide.

Embodiment 20: the embodiment of any of embodiments 1-19, wherein the adding step further comprises adding an effective amount of a molybdenum-containing compound to the antimony ammoxidation catalyst.

Embodiment 21: the embodiment of any of embodiments 1-20, wherein the molybdenum-containing compound comprises ammonium molybdates, metal molybdates, molybdenum oxides, or molybdenum acetates, or combinations thereof.

Embodiment 22: the embodiment of any of embodiments 1-21, wherein the antimony-containing compound comprises antimony triacetate, antimony oxides, or organoantimony compounds, or combinations thereof.

Embodiment 23: the embodiment of any of embodiments 1-22, wherein the adding further comprises adding at least one additive to the fluidized bed reactor.

Embodiment 24: An antimony-containing ammoxidation catalyst composition comprising: an antimony-containing ammoxidation catalyst; and an antimony-containing compound; wherein the antimony-containing compound has a melting point less than 375° C.

Embodiment 25: the embodiment of embodiment 23, wherein the antimony-containing compound comprises antimony triacetate.

Embodiment 26: the embodiment of embodiment 23 or 24, further comprising a molybdenum and a molybdenum-containing compound.

Embodiment 27: the embodiment of any of embodiments 23-25, wherein the molybdenum-containing compound comprises ammonium heptamolbydate.

Embodiment 28: A process for producing acrylonitrile, the process comprising: providing an antimony ammoxidation catalyst to a reactor; reacting propylene with ammonia and oxygen in the reactor in the presence of the antimony ammoxidation catalyst; measuring catalyst conversion of propylene and/or catalyst selectivity to acrylonitrile; and when conversion and/or selectivity is decreases, adding an effective amount of an antimony-containing compound to the antimony ammoxidation catalyst to maintain catalyst conversion and selectivity; wherein the antimony-containing compound has a melting point less than 375° C.

Embodiment 29: A process for stabilizing an antimony-containing catalyst in a reactor, the process comprising: providing an antimony-containing catalyst to a reactor; conducting a reaction in the presence of the antimony-containing catalyst, wherein the reaction is an ammoxidation reaction, or an oxidation reaction, or a combination thereof and adding an effective amount of an antimony-containing compound to the reactor.

Embodiment 30: the embodiment of embodiment 29, wherein the reaction is the ammoxidation reaction, and the reaction is conducted in the presence of ammonia and oxygen.

Embodiment 31: the embodiment of embodiments 29 or 30, wherein the reaction is oxidation reaction of a hydrocarbon feedstock, and the reaction is conducted in the presence of oxygen.

Embodiment 32: the embodiment of any of embodiments 29-31, wherein the hydrocarbon comprises olefins, alcohols, alkanes, ketones, aldehydes, carboxylic acids, esters, ethers, or nitriles, or derivatives thereof, or combinations thereof.

Embodiment 33: the embodiment of any of embodiments 29-32, wherein the adding further comprises adding a molybdenum-containing compound to the reactor.

The present disclosure is further understood by the following non-limiting examples.

EXAMPLES

Example 1

Figure 2:
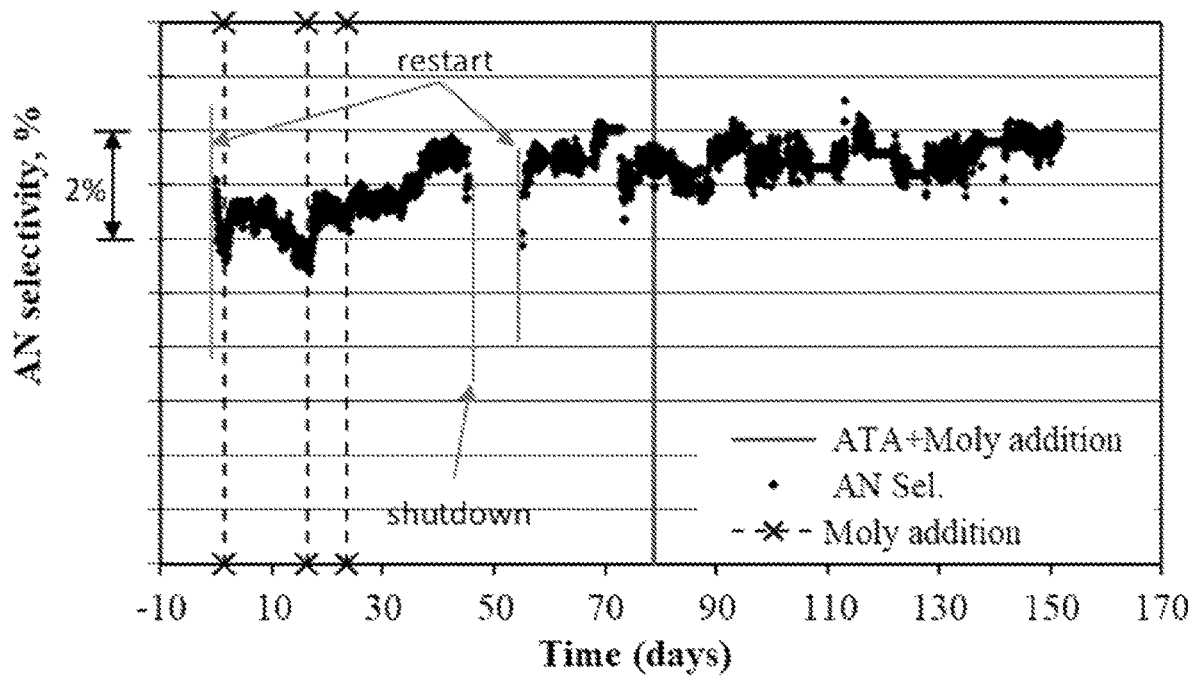
FIG. 2 shows the selectivity to acrylonitrile in accordance with embodiments of the present disclosure.
Figure 3:
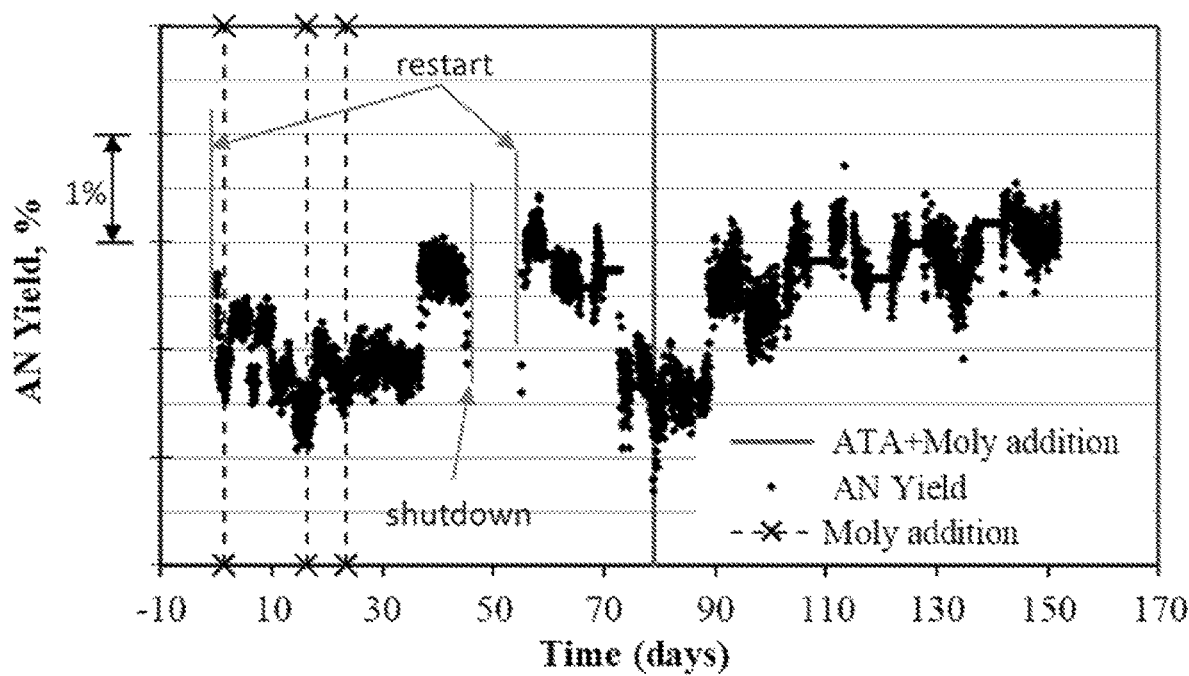
FIG. 3 shows the yield of acrylonitrile in accordance with embodiments of the present disclosure.

In order to form acrylonitrile, propylene, ammonia, and oxygen were fed to a reactor in the presence of an MAC-3 antimony ammoxidation catalyst. Over a period of approximately 150 days, propylene conversion, acrylonitrile selectivity, acrylonitrile yield, and propylene relative feed rate were measured. A molybdenum-containing compound was added at the first restart and then two additional times as indicated in FIGS. 1-3 by the dashed lines. After shutdown and restart, the reaction was allowed to run until propylene conversion, selectivity, and yield dropped to unacceptable levels. Then, a combination of antimony triacetate (825 ppm by weight) and the same molybdenum-containing compound as was previously added were added to the reactor through the hopper at approximately day 80. The results for the molybdenum-containing compound addition as well as the combination of antimony triacetate and the molybdenum-containing compound addition are shown in FIGS. 1-3. As used in this example, "restart" refers to a point where the reaction, which had previously been halted by stopping feeding of the reactants, is restarted by beginning to feed the reactants again. "Shutdown" refers to the point where the reactants are no longer being fed to the reactor.

As shown in FIG. 1, conversion of propylene began to decrease shortly after restart and a molybdenum-containing compound was added. After a slight increase, the conversion of propylene began to drop further. Two additional additions of the molybdenum-containing compound were made but as shown, the conversion continued to decrease. At restart, approximately at day 50, conversion was initially acceptable but then began to sharply decrease. At approximately day 80, when the combination of antimony triacetate and the molybdenum-containing compound were added, the conversion steadily increased and, on average, maintained at an acceptable conversion to approximately day 150. From FIG. 1, it is clear that the addition of antimony triacetate increased conversion of propylene.

As shown in FIG. 2, from restart at day 0 through the addition of the molybdenum-containing compound, selectivity increased. This increase in selectivity may be due to two factors: 1) the general trend that as conversion decreases, selectivity increases, and 2) that the molybdenum-containing compound had a positive effect on selectivity. The surprising and unexpected result of the antimony triacetate addition at approximately day 80 was that the general trend did not occur: instead of selectivity decreasing as conversion increased, selectivity also increased and maintained to approximately day 150. When FIGS. 1 and 2 are compared, the conversion and selectivity at day 80 and beyond, following the antimony triacetate addition, were superior to the results from days 0 to 50, where just the molybdenum-containing compound was added.

FIG. 3 provides the acrylonitrile yield which is calculated by multiplying propylene conversion by acrylonitrile selectivity. As shown in FIG. 3, the acrylonitrile yield was low at restart and remained low despite the molybdenum-containing compound addition. Following the second restart at approximately day 50, the yield rapidly decreased until the antimony triacetate was added. The addition of the antimony triacetate resulted in increased yield as compared to no addition of any compound and as compared to the addition of the molybdenum-containing compound alone.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that embodiments of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art.

We claim:

1. A process for producing acrylonitrile, the process comprising:
   providing an antimony ammoxidation catalyst to a reactor;
   reacting propylene with ammonia and oxygen in the reactor in the presence of the antimony ammoxidation catalyst;
   measuring catalyst conversion of propylene and/or catalyst selectivity to acrylonitrile; and
   when conversion and/or selectivity decreases, adding an effective amount of an antimony-containing compound to the antimony ammoxidation catalyst to maintain catalyst conversion and selectivity;
   wherein the antimony-containing compound has a melting point less than 375° C.

2. The process of claim 1, wherein the catalyst conversion is maintained within 10% of a target conversion over a period of at least 1 year.

3. The process of claim 1, wherein the catalyst selectivity to acrylonitrile is maintained within 10% of a target selectivity over a period of at least 1 year.

4. The process of claim 1, wherein the catalyst conversion is at least 45% over a period of at least 1 year.

5. The process of claim 1, wherein the catalyst selectivity to acrylonitrile is at least 50% over a period of at least 1 year.

6. The process of claim 1, wherein the antimony-containing compound is a solid.

7. The process of claim 1, wherein the adding is conducted at a temperature of less than 300° C.

8. The process of claim 1, wherein the antimony-containing compound comprises an antimony acetate.

9. The process of claim 1, further comprising the step of releasing antimony ammoxidation catalyst vapors from the antimony ammoxidation catalyst in the reactor.

10. The process of claim 9, further comprising the step of vaporizing the antimony-containing compound to suppress the release of the antimony ammoxidation catalyst vapors.

11. The process of claim 1, wherein the adding comprises mixing replenishing the antimony ammoxidation catalyst with the antimony-containing compound.

12. The process of claim 1, wherein further comprises:
   adding the antimony-containing compound directly into a catalyst hopper comprising replenishing antimony ammoxidation catalyst and then feeding the resultant replenished antimony catalyst composition to the reactor;
   mixing the antimony-containing compound with the antimony ammoxidation catalyst and then feeding the resultant replenished antimony catalyst composition directly to the reactor;
   dissolving antimony-containing compound in water to form an aqueous solution and then adding the aqueous solution to the reactor; or
   combinations thereof.

13. The process of claim 1, wherein the antimony-containing compound and the antimony ammoxidation catalyst comprises less than 1 wt % potassium, lithium, sodium, cesium, indium, rubidium, samarium, calcium, strontium, barium or tellurium.

14. The process of claim 1, wherein the antimony ammoxidation catalyst further comprises molybdenum and/or a molybdenum oxide.

15. The process of claim 1, wherein the adding step further comprises adding a molybdenum-containing compound to the antimony ammoxidation catalyst.

16. The process of claim 1, wherein the antimony-containing compound comprises antimony triacetate, antimony oxides, or organoantimony compounds, or combinations thereof.

17. The process of claim 1, wherein the adding further comprises adding at least one additive to the reactor, wherein the reactor is a fluidized bed reactor.

* * * * *